United States Patent
Yang

(10) Patent No.: US 7,572,412 B2
(45) Date of Patent: Aug. 11, 2009

(54) AROMA LAMP

(76) Inventor: Chin-Sheng Yang, 4F., No. 26, Lane 358, Yung-An St., Tainan City (TW)

( * ) Notice: Subject to any disclaimer, the term of this patent is extended or adjusted under 35 U.S.C. 154(b) by 0 days.

(21) Appl. No.: 12/238,460

(22) Filed: Sep. 26, 2008

(65) Prior Publication Data

US 2009/0123345 A1 May 14, 2009

(30) Foreign Application Priority Data

Nov. 12, 2007 (TW) .............................. 96219031 U

(51) Int. Cl.
*A61L 9/02* (2006.01)
(52) U.S. Cl. ..................... 422/124; 422/5; 422/120; 422/123; 392/386; 392/393
(58) Field of Classification Search ............... 422/5, 422/120, 123, 124, 125; 392/386, 390, 393
See application file for complete search history.

(56) References Cited

U.S. PATENT DOCUMENTS

| | | | | |
|---|---|---|---|---|
| 4,816,973 A | * | 3/1989 | Atalla et al. ........ | 362/643 |
| 6,106,786 A | * | 8/2000 | Akahoshi ............ | 422/124 |
| 6,413,476 B1 | * | 7/2002 | Barnhart ............. | 422/124 |
| 2006/0258215 A1 | * | 11/2006 | Lai et al. ............. | 439/607 |

\* cited by examiner

*Primary Examiner*—Sean E Conley
(74) *Attorney, Agent, or Firm*—Leong C. Lei

(57) ABSTRACT

The aroma lamp contains a base member having a circuit member and a Universal Serial Bus (USB) connector. A fan module is positioned facing upward on a top surface of the base member. A hollow support member covers the top surface of the base member and the fan module. The support member has a vertical tube with surrounding openings which penetrates an aroma producing element and a light generating element is positioned at a top end of the vertical tube. A hollow lamp shade is detachably joined to the support member and houses the aroma producing element and the light generating element inside. When the USB connector is connected to a computer, the fan module is turned on and drives air to flow upward against the aroma producing element. The aroma producing element vaporizes and the aroma is spread outside the lamp shade.

5 Claims, 4 Drawing Sheets

AROMA LAMP

TECHNICAL FIELD OF THE INVENTION

The present invention generally relates to aroma or fragrance producing devices, and more particularly to an aroma lamp receiving its power through a Universal Serial Bus (USB) connection.

DESCRIPTION OF THE PRIOR ART

There are various commercially available devices for removing unpleasant odors from the environment, from pets, from dirty clothes, etc. For example, there are incense burning devices, deodorant spraying devices, ethereal oil burning devices, to name just a few. Recently, the ethereal oil burning devices are especially popular as aroma therapy receives wide acceptance as an effective healing and relaxing means.

There are also products combining a night lamp and an ethereal oil burning device together. These products are usually plugged into a wall outlet and use a light bulb of small wattage for illumination. The heat produced by the light bulb is also used in evaporating ethereal oil to produce pleasant fragrance.

SUMMARY OF THE INVENTION

A novel aroma lamp is provided here which simultaneously provides illumination and aroma. The aroma lamp contains a base member having a circuit member and a Universal Serial Bus (USB) connector. A fan module is positioned facing upward on a top surface of the base member. A hollow support member covers the top surface of the base member and the fan module. The support member has a vertical tube with surrounding openings which penetrates an aroma producing element and a light generating element is positioned at a top end of the vertical tube. A hollow lamp shade is detachably joined to the support member and houses the aroma producing element and the light generating element inside.

When the USB connector is connected to a computer, the fan module is turned on by the electricity drawn through the USB connector. The fan module drives air to flow upward against the aroma producing element. The aroma producing element vaporizes and the aroma is spread outside the lamp shade via a top opening of the lamp shade.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
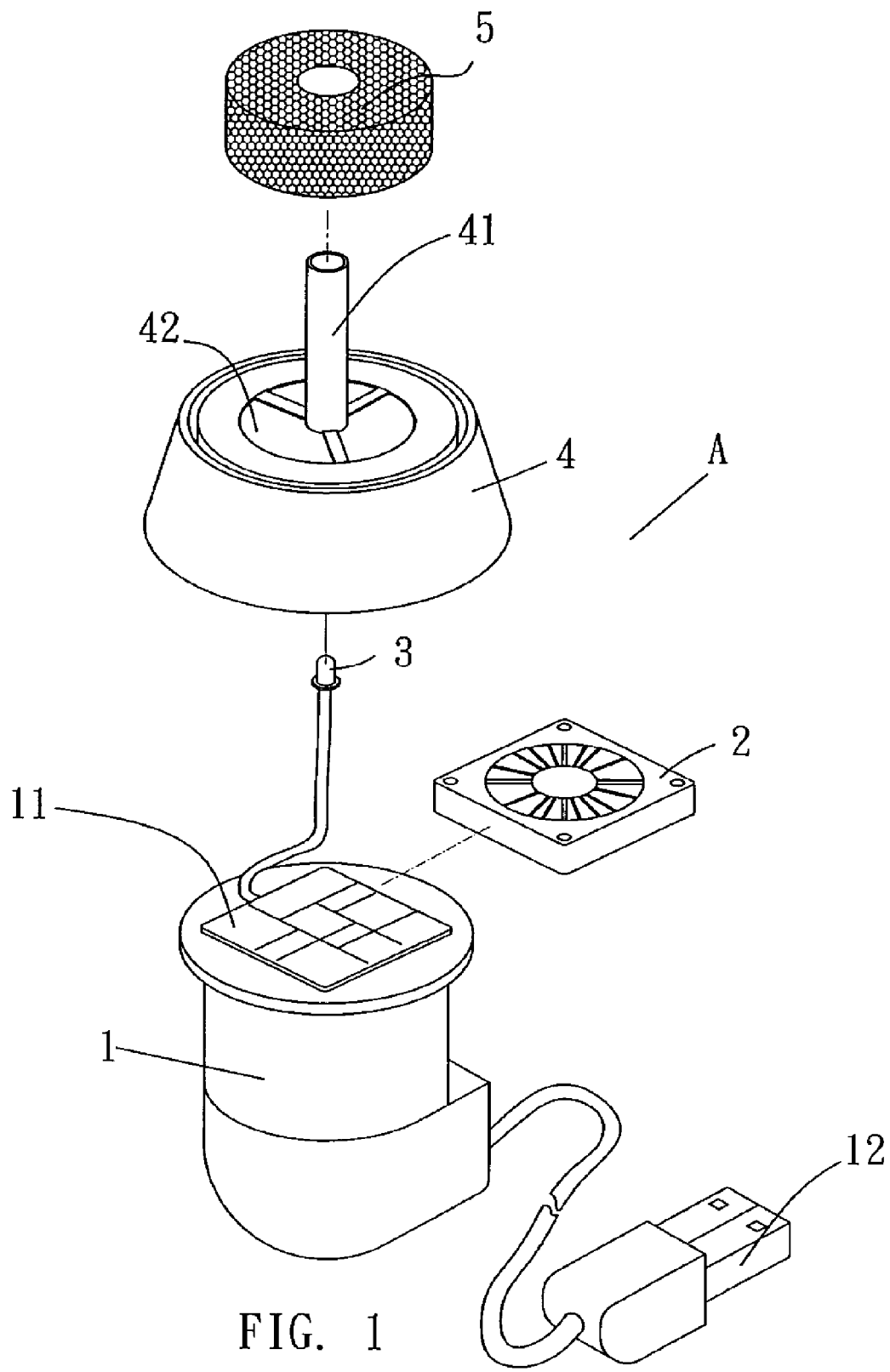
FIG. 1 is a perspective diagram showing the various components of an aroma lamp according to an embodiment of the present invention.
Figure 2:
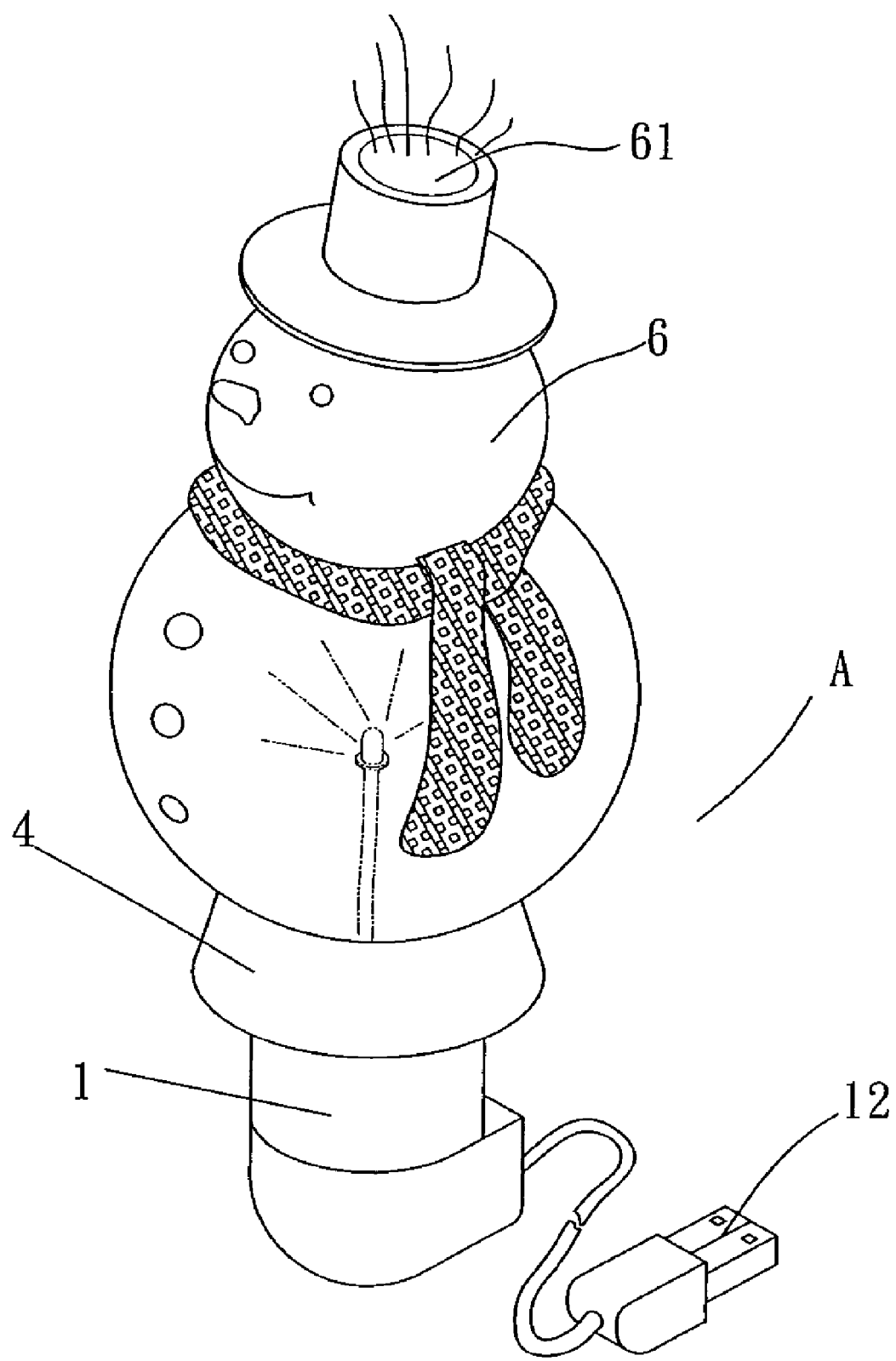
FIG. 2 is a perspective diagram showing the aroma lamp of FIG. 1 after its assembly and with a lamp shade installed.

As shown in FIGS. 1 and 2, an aroma lamp A according to an embodiment of the present invention mainly contains a base member 1 having a circuit member 11 and a Universal Serial Bus (USB) connector 12. By plugging the USB connector 12 to an electronic device such as a personal or notebook computer, the aroma lamp A draws electricity from the electronic device to power the circuit member 11 and other components.

A fan module 2 is positioned facing upward on a top surface of the base member 1 and is connected to the circuit member 11. When the fan module 2 is turned on, it will produce air flow along a vertical direction.

A light generating element 3 such as a light emitting diode is connected to the circuit member 11 and is positioned above the fan module 2.

The aroma lamp A further contains a hollow support member 4 which covers the top surface of the base member 1 and the fan module 2. The support member 4 has a vertical tube 41 allowing the light generating element 3 to thread through. Surrounding the vertical tube 41, the support member 4 has a number of openings 42 allowing air to flow through.

An aroma producing element 5 is supported by the support member 4 and is positioned right above the openings 42 with the vertical tube 41 penetrating through the aroma producing element 5.

A hollow lamp shade 6 is joined to the support member 4 and houses the aroma producing element 5 and the light generating element 3 inside. There is an opening 61 on a top side of the lamp shade 6 to allow air flow.

Figure 3:
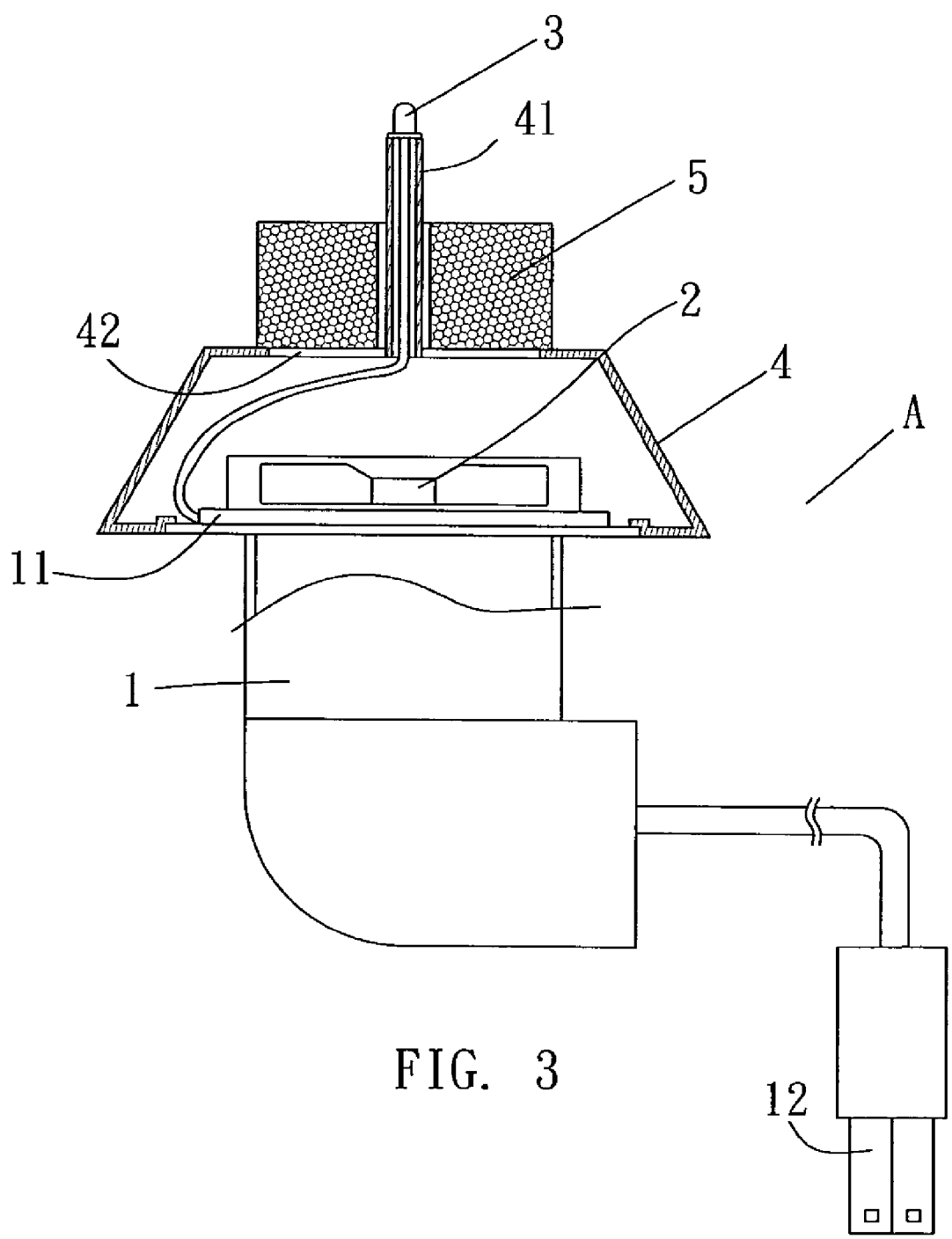
FIG. 3 is a sectional diagram showing the aroma lamp of FIG. 1.
Figure 4:
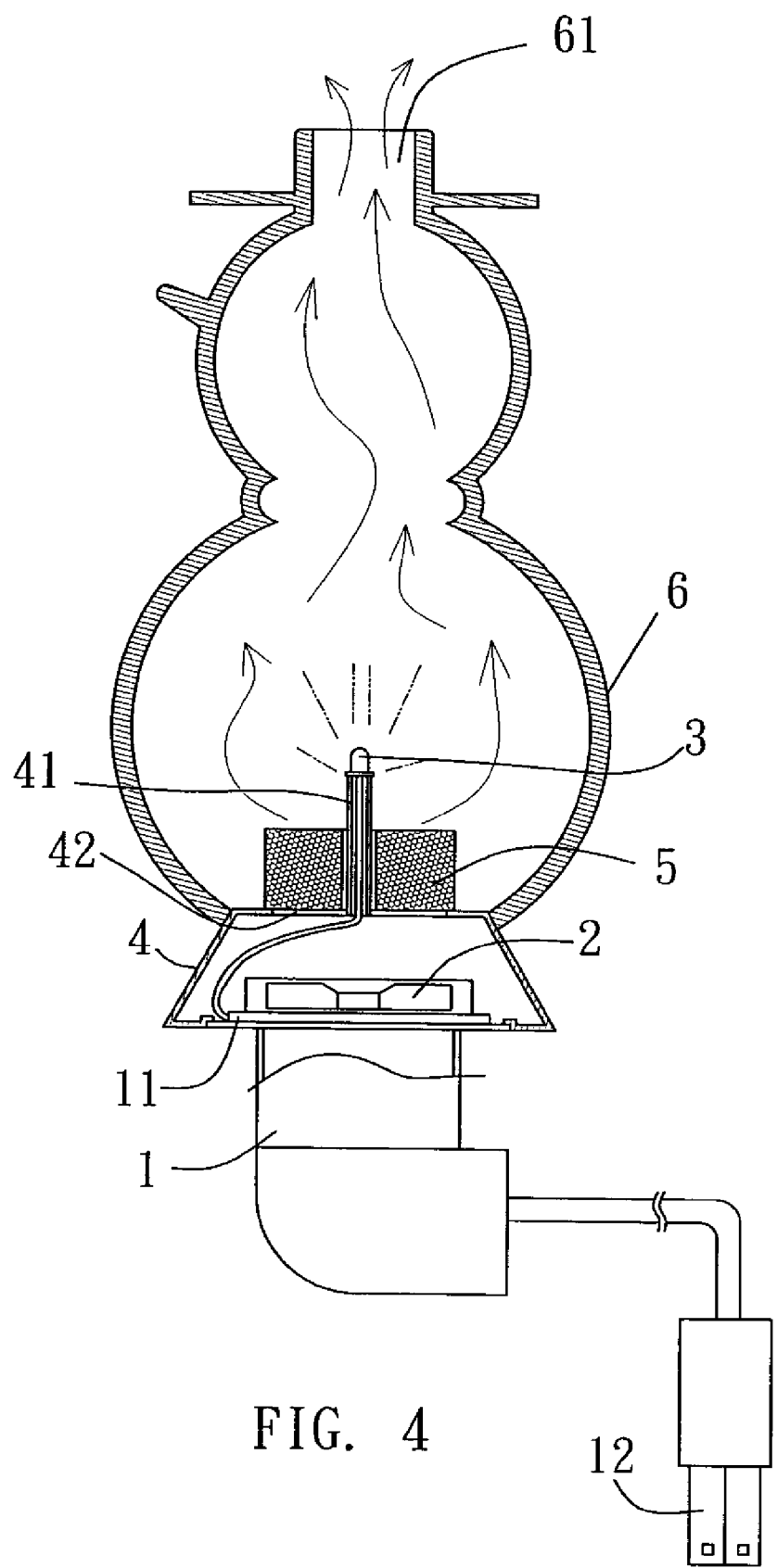
FIG. 4 is a sectional diagram showing the aroma lamp of FIG. 2.

As also shown in FIGS. 3 and 4, when the USB connector 12 is connected to a computer, the fan module 2 is turned on by the electricity drawn through the USB connector 12. The fan module drives air to flow upward against the aroma producing element 5 via the openings 42. The aroma producing element 5 vaporizes and the aroma is spread outside the lamp shade 6 via its top opening 61. The aroma producing element 5 could be a sponge soaked with ethereal oil or a soap made of solidified ethereal oil. When the USB connector 12 is connected to a computer, the light generating element 3, positioned generally in the center of the lamp shade 6, is also turned on to provide illumination.

Please note that the lamp shade 6 could have various visually appealing shapes. The lamp shade 6 is detachably joined to the support member 4 and could be removed easily so that the support member 4 and the base member 1 are used by themselves. The details to the circuit member 11 should be straightforward to people of related arts and are therefore omitted here.

As described above, the aroma device of the present invention simultaneously provides illumination and aroma. It uses a vaporizable aroma producing element as the source of aroma and uses a fan module to facilitate its vaporization and the delivery of aroma. The illumination is provided by a light emitting diode which consumes very little power and generate minimum amount of heat.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An aroma lamp, comprising:
   a base member having a circuit member inside and a Universal Serial Bus (USB) connector;
   a fan module on a top surface of said base member connected to said circuit member, said fan module producing air flow along a vertical direction;
   a hollow support member joined to said base member to cover said top surface of said base member and said fan module, said support member having a vertical tube and a plurality of openings surrounding said vertical tube to allow air to flow through;
   an aroma producing element supported by said support member and positioned above said openings, said vertical tube penetrating said aroma producing element;
   a light generating element positioned at a top end of said vertical tube and connected to said circuit member via said vertical tube; and
   a hollow lamp shade joined to said support member to house said aroma producing element and said light generating element inside, said lamp shade having a top opening;
   wherein said circuit member, said light generating element, and said fan module are powered by electricity drawn through said USB connector; when said the fan module is turned on by the electricity drawn through said USB connector, said fan module drives air to flow upward against said aroma producing element via said openings; said aroma producing element vaporizes and aroma is spread outside said lamp shade via said top opening.

2. The aroma lamp according to claim 1, wherein said aroma producing element is a sponge soaked with ethereal oil.

3. The aroma lamp according to claim 1, wherein said aroma producing element is a soap made of ethereal oil.

4. The aroma lamp according to claim 1, wherein said light generating element is a light emitting diode.

5. The aroma lamp according to claim 1, wherein said lamp shade and said support member are detachable.

* * * * *